US006897651B2

(12) United States Patent
Reiderman et al.

(10) Patent No.: US 6,897,651 B2
(45) Date of Patent: May 24, 2005

(54) METHOD FOR ELIMINATING EFFECTS OF ACOUSTIC EXCITATIONS IN NMR DATA

(75) Inventors: Arcady Reiderman, Houston, TX (US); David R. Beard, Houston, TX (US); Zinovy B. Krugliak, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 0 days.

(21) Appl. No.: 10/439,100

(22) Filed: May 15, 2003

(65) Prior Publication Data

US 2004/0232915 A1 Nov. 25, 2004

(51) Int. Cl.[7] ................................................ G01V 3/00
(52) U.S. Cl. ...................................... 324/303; 324/306
(58) Field of Search ................................. 324/303, 306, 324/307, 309, 300

(56) References Cited

U.S. PATENT DOCUMENTS

| 4,698,979 A | 10/1987 | McGuigan | 62/171 |
| 4,710,713 A | 12/1987 | Strikman | 324/303 |
| 5,055,787 A | 10/1991 | Kleinberg et al. | 324/303 |
| 5,712,566 A | 1/1998 | Taicher et al. | 324/303 |
| 6,121,774 A | * 9/2000 | Sun et al. | 324/303 |
| 6,204,663 B1 | 3/2001 | Prammer | 324/303 |
| 6,541,969 B2 | 4/2003 | Sigal et al. | 324/303 |
| 6,570,381 B1 | * 5/2003 | Speier et al. | 324/303 |

FOREIGN PATENT DOCUMENTS

EP 0967490 A2 12/1999

* cited by examiner

*Primary Examiner*—Louis Arana
(74) *Attorney, Agent, or Firm*—Madan, Mossman & Sriram, P.C.

(57) ABSTRACT

The invention is a method of reducing the effects of non-formation signals in an NMR logging echo signal obtained within a borehole in an earth formation. The method obtains a non-formation signal by the application of at least an excitation pulse, and preferably also at least one refocusing pulse. The obtained signal is used to numerically construct a synthetic ringing signal sequence. The constructed signal can then be subtracted from an NMR echo signal to reduce the effects of ringing.

34 Claims, 6 Drawing Sheets

METHOD FOR ELIMINATING EFFECTS OF ACOUSTIC EXCITATIONS IN NMR DATA

BACKGROUND OF THE INVENTION

1. Field of the Invention

The present invention relates to improved signal determination in nuclear magnetic resonance well logging. More specifically, the invention is a method directed towards eliminating spurious effects of magneto-acoustic ringing from obtained resonance signals.

2. Description of the Related Art

Nuclear magnetic resonance (NMR instruments have been adapted for use in wellbores drilled through earth formations. Generally speaking, NMR instruments used for analyzing earth formations include a magnet for inducing a static magnetic field in the earth formations to be evaluated, an antenna placed proximate to the formations to be analyzed, and circuitry adapted to conduct radio-frequency (RF) power pulses through the antenna to induce an RF magnetic fields in the same formations. The circuitry also includes a receiver adapted to detect signals induced in the antenna (or a separate receiving antenna). The induced signals are related to NMR phenomena induced in the formation of interest by the combined action of the static magnetic field and the RF magnetic field.

Typically, measurement of NMR related phenomena in the earth formation is performed by introducing a static magnetic field $B_0$ and allowing some time for the static magnetic field to polarize nuclear spins in the formation in a direction substantially along the direction of the static magnetic field. Bb may be produced by one or more permanent magnet or electromagnets. An oscillating magnetic field $B_1$ may be produced by one or more RF antennas to excite and detect nuclear magnetic resonance. A typical sequence of RF pulses is known as the Carr-Purcell-Meiboom-Gill (CPMG) sequence. The first RF pulse of this sequence is known as the excitation pulse has a magnitude and duration selected to reorient the nuclear magnetization by about 90 degrees from its previous orientation. After a selected time, successive RF pulses, known as refocusing pulses, are passed through the antenna. Each of these pulses typically has a magnitude and duration selected to reorient the nuclear spin axes by about 180 degrees from their immediately previous orientations. Each refocusing pulse enables the nuclear spin axes to "rephase" or realign with each other. After application of an RF pulse, the magnetization begins to precess around $B_0$ and produces a detectable signal in the antenna. The induced signals, known as "spin echoes", are generally measured during the time interval between each successive refocusing pulse. The amplitude of the spin echo signals, and the rate at which the spin echo amplitudes change during a measurement sequence, are related to properties of interest of the earth formations, such as fractional volume of pore space (porosity) and the properties of fluids present in the pore spaces. The frequency of the RF magnetic field needed to reorient the nuclear magnetization, is equal to the Larmor frequency a $\omega_0 = \gamma B_0$ where $\gamma$ is the gyromagnetic ratio. For evaluation of earth formations, the static magnetic field amplitude and RF magnetic field frequency are typically selected to excite NMR phenomena in hydrogen nuclei, although other nuclei may be used for NMR evaluation of earth formations.

Exciting the antenna with RF power pulses in the presence of a strong static magnetic field causes mechanical excitation of the antenna. Mechanical excitation of the antenna leads to excitation of a signal, called "ringing", in the antenna. This phenomenon can be explained as follows: The RF magnetic field induces eddy currents within the skin depth of the metal. In the presence of a static magnetic field, the electrons experience a Lorentz force. This same force affects the lattice as well, causing the acoustic waves. As discussed in Buess et al. (see M. L. Buess and G. L. Petson. Rev. Sci. Instrum. 49(8), 1978.), the ionic displacement is proportional to the strength of the RF magnetic field at the surface of the metal. A reciprocal mechanism converts acoustic waves into oscillating RF magnetic fields, which thereby induces voltage in the NMR receiver coil.

Another source of the magneto-acoustic ringing is generation of ultrasonic waves in non-conductive magnetic materials via the process of magneto-striction. The non-conductive magnetic material, typically ferrite, can be used as a permanent magnet, as discuss in Taicher '713 (U.S. Pat. No. 4,710,713). Alternatively, the magnetic material can be used as the antenna core, as discussed in Taicher '979 (U.S. Pat. No. 4,698,979) and Kleinberg '787 (U.S. Pat. No. 5,055,787). In these uses also, the inverse effect causes the magnetization oscillations to induce voltage in the NMR receiver. The effect is also linearly proportional with respect to the RF magnetic: field at the surface of the magnetic material.

The ringing is unrelated to NMR phenomena, and frequently has a very large amplitude. The amplitude of the ringing is often highest right after application of each RF pulse, and is of such a magnitude as to make it difficult to measure the amplitude of induced NMR signals. Reducing the effect, of ringing on NMR measurement is very important in well logging applications, among others, because significant information about the properties of the earth formations are determined by the amplitudes of spin echoes occurring shortly after the RF pulses.

Several methods are known in the art for reducing ringing. One device for reducing ringing is to have the magnet arranged so as to dispose the antenna in a region having substantially zero static magnetic field amplitude. An NMR apparatus which has this arrangement is described, for example, in U.S. Pat. No. 5,712,566 issued to Taicher. Yet another device for reducing ringing is to provide separate antennas for inducing the RF magnetic field and detecting the NMR induced signals, where these two antennas are substantially orthogonal to each other. Ringing induced in the transmitting antenna is substantially undetected by the receiving antenna. See for example, the Taicher '566 patent referred to previously.

A standard technique for suppressing the magneto-acoustic ringing due to an applied CPMG sequence includes repeating the measurement with the RF phase of the excitation pulse inverted. Thus the NMR pulse sequence is implemented in the form of phase alternated pairs (PAPs): where TW is the wait time, $90_{\pm x}$ is the excitation pulse with RF carrier phase alternated, $B_y$ is the refocusing pulse, $t_{cp}=TE/2$ is half of the echo spacing (TE). As a result of this alternation, the NMR signal inverts the phase of the echoes but leaves unaffected the ringing signal. As a preferred option of operation, the refocusing pulse $B_y$ is a 180° pulse. The ringing signal can be eliminated from a pair of phase alternated CPMG sequences by subtracting the echo signal generated by one CPMG sequence from the echo signal generated by another CPMG sequence within the alternated pair. The subtractions eliminates ringing caused by the refocusing pulses and also eliminates a DC offset of the receiver.

One shortcoming of the PAP approach is that it does not eliminate ringing due to the excitation pulse. Since the ringing signal due to the excitation pulse inverts its phase the same way as the echo signal, it can not be subtracted using the method of alternated pairs. As a result, this ringing typically corrupts the first one or two echoes in the CPMG sequence, thereby affecting the resolvability of the fast relaxation components in the NMR relaxation spectrum.

A method of eliminating the ringing due to the excitation pulse is described in U.S. Pat. No. 6,204,663, issued to Prammer. The method of Prammer '663 is based on changing the measurement frequency between certain pulse sequences and averaging out data points obtained from the different sequences in a way that effectuates cancellation of the spurious signals. Since mechanical resonance producing an acoustic ringing occurs at its own frequency, the ringing signal will change its phase with respect to the changed NMR signal. If the frequency change is made equal to one-half of the time between excitation pulse and acquisition, an additional phase difference of 180 degrees between ringing signals in two sequences can be achieved. Then, adding the signals from the two measurements eliminates ringing from the excitation pulse. A drawback of this approach is that the width of the acquisition window may be comparable with TE, so the ringing subtraction can not be achieved over the entire echo acquisition window. The method of Prammer '663 is difficult to implement if there is a substantial excitation pulse ringing signal in the second echo acquisition window.

U.S. Pat. No. 6,541,969 B2, issued to Sigal et al., discusses a method and system for improving the resolution of bore hole NMR logging measurements and for suppressing artifacts in NMR data obtained from logging measurements. In a preferred embodiment, the NMR pulse echo trains are CPMG spin echo trains. Further, non-formation signal contribution is estimated from two or more of the plurality of CPMG spin echo trains, preferably using one or more phase-alternated pair(s) of CPMG spin echo trains. In a specific implementation to PAPs are used that are formed by a current CPMG spin echo train ($CPMG_0$) and an immediately preceding ($CPMG_{-1}$) and an immediately following ($CPMG_{+1}$) phase alternated CPMG spin echo trains. In another embodiment, non-formation signal contribution is estimated using a separate NMR pulse echo train, which preferably is a CPMG spin echo train without an initial $\pi/2$ (excitation) pulse.

Another problem of the PAP approach as applied to NMR with logging arises from the inherent delay between sequences in the alternated pairs. Since the NMR device moves through the borehole during this delay, the echoes from the CPMG sequence can be measured in two environments having two different conductivities. Thus, the antenna response to the signal generated by magneto-acoustic effects can be different between the first and second obtained signal, and the ringing subtraction can become inaccurate as a result.

A technique addressing this problem is described in EP 0967490 A2, issued to Sun et al. Rather than employing PAPs, the method obtains a main signal comprising spin echo signals and undesired effects and then subtracts a signal from a second time period having only the undesired effects. Following the main part of the CPMG pulse sequence comprising echo signal, ringing and DC offset, the spin echoes are eliminated by using, for example, a missing 180° pull technique. The continuation of the allows for acquiring the ringing and DC offset only. The ringing and DC offset acquired during the second part of the sequence is averaged and then subtracted from the signal acquired during the main part. One drawback to this technique is that it consumes a substantial amount of DC power, and power consumption is critical for NMR well logging. Another drawback is related to the procedure employed for averaging the ringing signal, which operates using the assumption that the ringing signal repeat itself from echo to echo. This is not typically the case. Thus, the calculated average signal may not represent the ringing signal in a few first echo acquisition windows There is a need to develop a method that reduces the effect of magneto-acoustic ringing in NMR experiments in a manner that minimally extends power consumption and can be operated in a region that sufficiently approximates the region in which signal detection occurs. The method of this invention addresses those needs.

SUMMARY OF THE INVENTION

The present invention is a method of reducing the effects of non-formation; signals in a nuclear magnetic resonance (NMR) echo signal obtained within a borehole in an earth formation. The method of the invention obtains an NMR echo signal sequence in response to a primary applied pulse sequence as well as at least one auxiliary signal pertaining to non-formation signal. The NMR echo signal typically carries formation and non-formation signals. The at least one auxiliary signal is in response to a single auxiliary pulse sequence applied at substantially the same depth as the primary pulse sequence and having at least an excitation pulse. The auxiliary sequence carries information on the non-formation signals. A sequence of signal responses is constructed from the at least one auxiliary signal in order to simulate the effective non-formation signal. The constructed signal is then subtracted from the NMR echo signal sequence.

The primary pulse sequence of the invention is preferably a Carr-Purcell-Meiboom-Gill (CPMG) pulse sequence, having an excitation pulse following by a plurality of refocusing pulses. Preferably, the refocusing pulse of the primary pulse sequence further comprises a 180° reorientation pulse. Alternatively, the refocusing pulse can be of a length for reorienting atomic nuclei by an angle in a range between 90° and 180°.

The auxiliary pulse sequence comprises at least an excitation pulse of the CPMG sequence and preferably further comprises act least one refocusing pulse. Preferably, the auxiliary pulse sequence is of the form $$TW_a-90_{\pm x}-(t_{cpa}-B_y-t_{cpa})_{N_a}-90_{\mp x}$$

where $TW_a$ waiting time before the start of the auxiliary train; $90_{\pm x}$ is an excitation pulse with RF carrier phase alternated; $t_{cpa}$ is the time interval between the excitation and refocusing pulses of the auxiliary pulse; $B_y$ is the refocusing pulse; $90_{\mp x}$ is a forced recovery pulse; and $N_a$ is the number of repetitions in the auxiliary train. The auxiliary pulse sequence is typically applied after a short time period ($TW_a$) after the end of the primary pulse sequence. The refocusing pulse ($B_y$) of the auxiliary pulse sequence can comprise a 180° reorientation pulse. Alternatively, the refocusing pulse of the auxiliary pulse can be a pulse for reorienting atomic nuclei by an angle in a range between 90° and 180°.

DESCRIPTION OF PREFERRED EMBODIMENT

Figure 1:
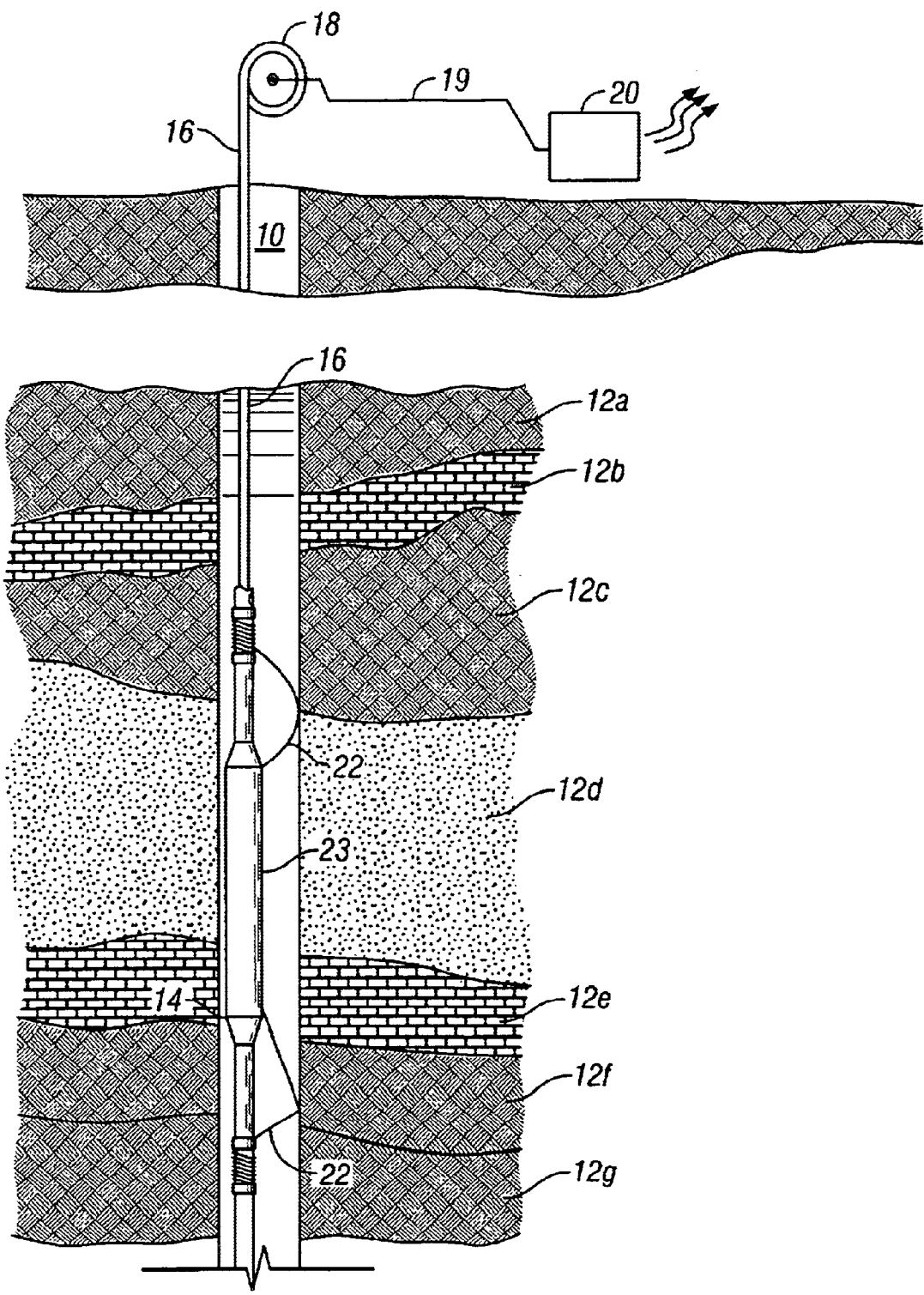
FIG. 1 shows a well logging instrument suitable for use with the present invention.

FIG. 1 depicts a borehole 10 which has been drilled in a typical fashion into a subsurface geological formation 12 to be investigated for potential hydrocarbon producing reservoirs. An NMR logging tool 14 has been lowered into the hole 10 by means of a cable 16 and appropriate surface equipment represented diagrammatically a reel 18 and is being raised through the formation 12 comprising a plurality of layers 12a through 12g of differing composition, to log one or more of the formation's characteristics. The NMR logging tool is provided with bowsprings 22 to maintain the tool in an eccentric position within the borehole with one side of the tool in proximity to the borehole wall. The permanent magnets used for providing the static magnetic field is indicated by 23 and the magnet configuration is that of a line dipole. Signals generated by the tool 14 are passed to the surface through the cable 16 and from the cable 16 through another line 19 to appropriate surface equipment 20 for processing, recording and/or display or for transmission to another site for processing, recording and/or display.

Figure 2:
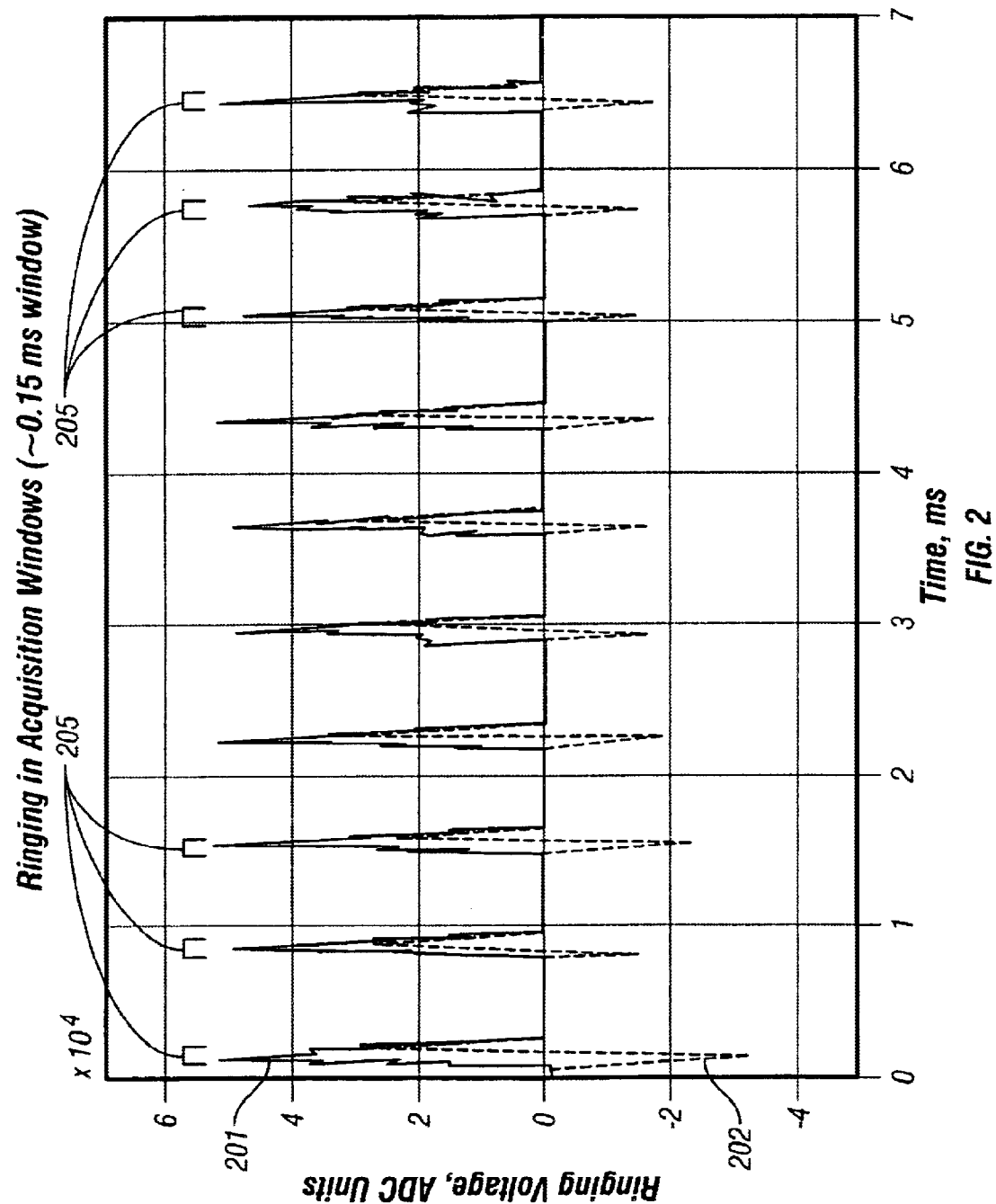
FIG. 2 shows the ringing signal captured in a plurality of acquisition windows corresponding to a CPMG sequence.

FIG. 2 shows a plurality of ringing signals captured in a plurality of acquisition windows 205 corresponding to a CPMG sequence. Each acquisition window 205 has a duration of 0.15 ms. Acquisition windows are separated by the time interval TE=0.7 ms. Time is displayed in FIGS. 2–6 along the: abscissa in units of ms and the ringing is displayed along the ordinate on the scale of $10^{-4}$ ADC units of voltage. The solid line 201 corresponds to the in-phase channels of the quadrature detector normally used in the NMR receivers. The dotted line 202 corresponds to the out-of-phase channel signal. The two signals can be considered as the real and imaginary parts of the complex vector representing the output voltage. Data in FIG. 2 is obtained with no hydrogen-containing sample coupled with the probe.

It is known that the amplitude of the acoustic excitation, produced either by an RF magnetic field in metal or by an applied electric field in dielectric material, follows a linear relation with respect to the RF field amplitude (see, for example, Buess et al.). A reasonable approximation can be made wherein the spurious signal, acquired in the NMR antenna in response to this acoustic excitation, is also linear with RF magnetic field strength. Thus, the ringing signal in the CPMG experiment can be reconstructed using the superposition principle given that the ringing signal from the excitation RF pulse and from a single refocusing RF pulse are known. The ringing signal in the echo acquisition window can be calculated according to the following equation:

$$R_{X,Y}(t) = W(t) \cdot \left[ R_{90X,Y}(t) + \sum_{i=1}^{N} R_{BX,Y}(t - TE/2 - (i-1) \cdot TE) \right] \quad (2)$$

with t>TE/2+(i−1)·TE, and where $R_{90X,Y}(t)$ is the ringing signal after the excitation pulse with t=0 corresponding to the center of the pulse; $R_{BX,Y}(t-TE/2-(i-1)TE)$ is the ringing signal obtained after application of the $i^{th}$ refocusing pulse; W(t) is the acquisition window function; N is the number of refocusing pulses used for the ringing signal acquisition; TE=$2t_{cp}$ is the time interval between the refocusing pulses. The width of the refocusing pulse is discussed in U.S. Pat. No. 6,163,153, issued to Reiderman et al., the contents of which are incorporated herein by reference. In a preferred mode of the invention, the ringing from the refocusing pulse $R_{BX,Y}$ is due to application of a 180° refocusing pulse. In an alternative, the refocusing pulse can lie within a range of, for example, a 90° pulse and a 180° pulse. Alternatively, the ringing signal due to the refocusing pulse can be determined by using the ringing from the excitation pulse.

The ringing constructed according to Eq. (2) is to be subtracted from the measured signal. In order to acquire ringing for $R_{90X,Y}(t)$ and $R_{BX,Y}(t)$, an auxiliary pulse train containing at least one excitation and one refocusing pulse is employed. The TE used in the auxiliary train should be greater than that of the pulse train employed for the main NMR experiment in order to move the spin echo signal out of the ringing acquisition interval, thereby isolating the ringing effect. A plurality of refocusing pulses may be employed in the auxiliary train for the purpose of increasing the signal-to-noise ratio (SNR) through stacking of the ringing data. The time interval between refocusing pulses is preferably set to at least 3(TE+$\tau_B$), where $\tau_B$ is the refocusing pulse width used to isolate ringing effects.

Figure 3:
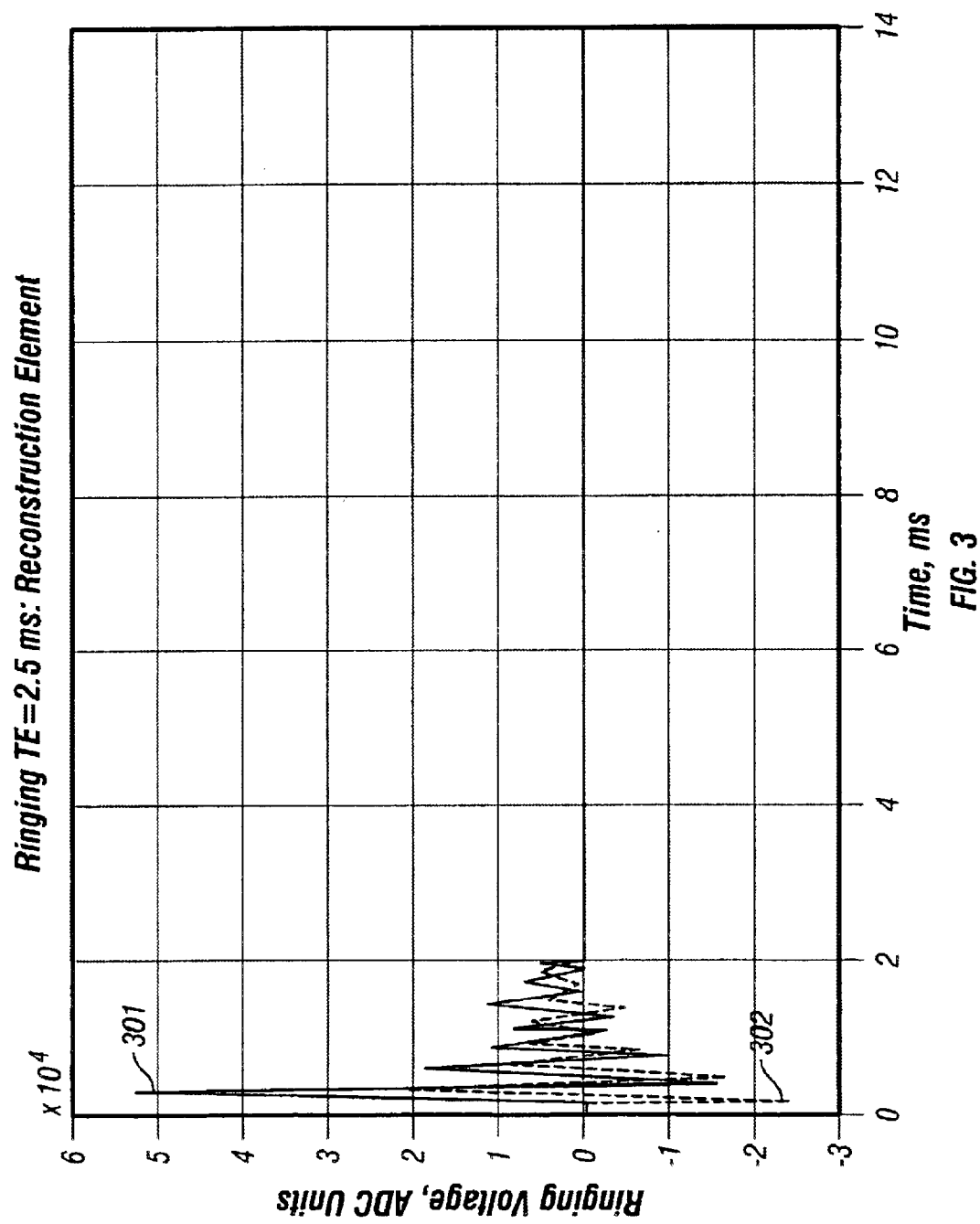
FIG. 3 shows the ringing signal after a single refocusing RF pulse.

FIG. 3 shows a ringing signal obtained after the application of a single refocusing RF pulse. A single acquisition window is used. The duration of the acquisition window for the single pulse ringing shown in FIG. 3 is 2 ms. The solid line 301 represents the in-phase component of the signal, and the broken line 302 represents the out-of-phase component of the signal.

Figure 4:
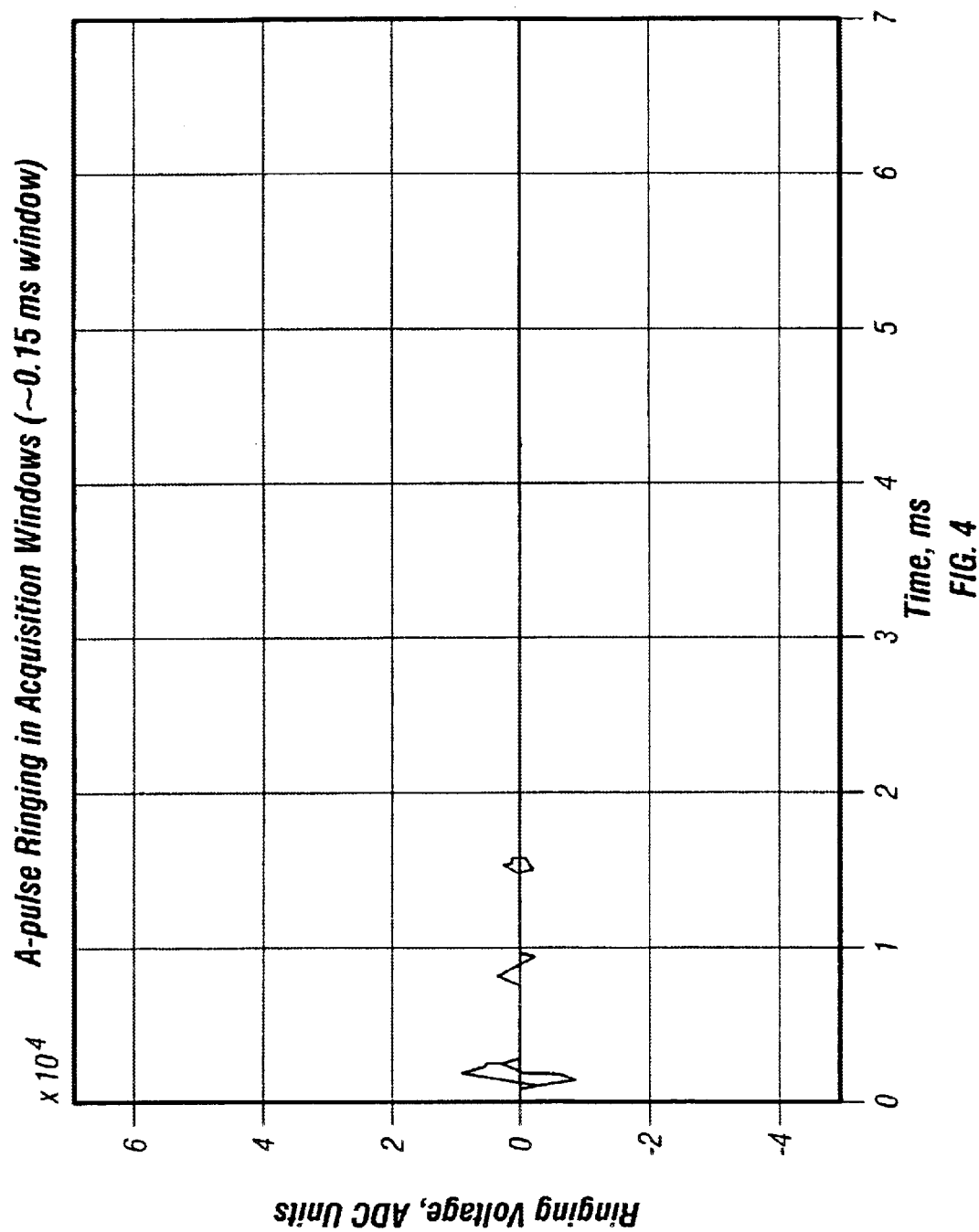
FIG. 4 shows the ringing signal after an excitation pulse.

FIG. 4 shows the ringing signal after the application of a single excitation pulse. The signal as shown is captured in acquisition windows for the first three echoes of a CPMG experiment. Acquisition intervals leave a duration of 0.15 ms and are spaced at an interval of TE=0.7 ms.

Figure 5:
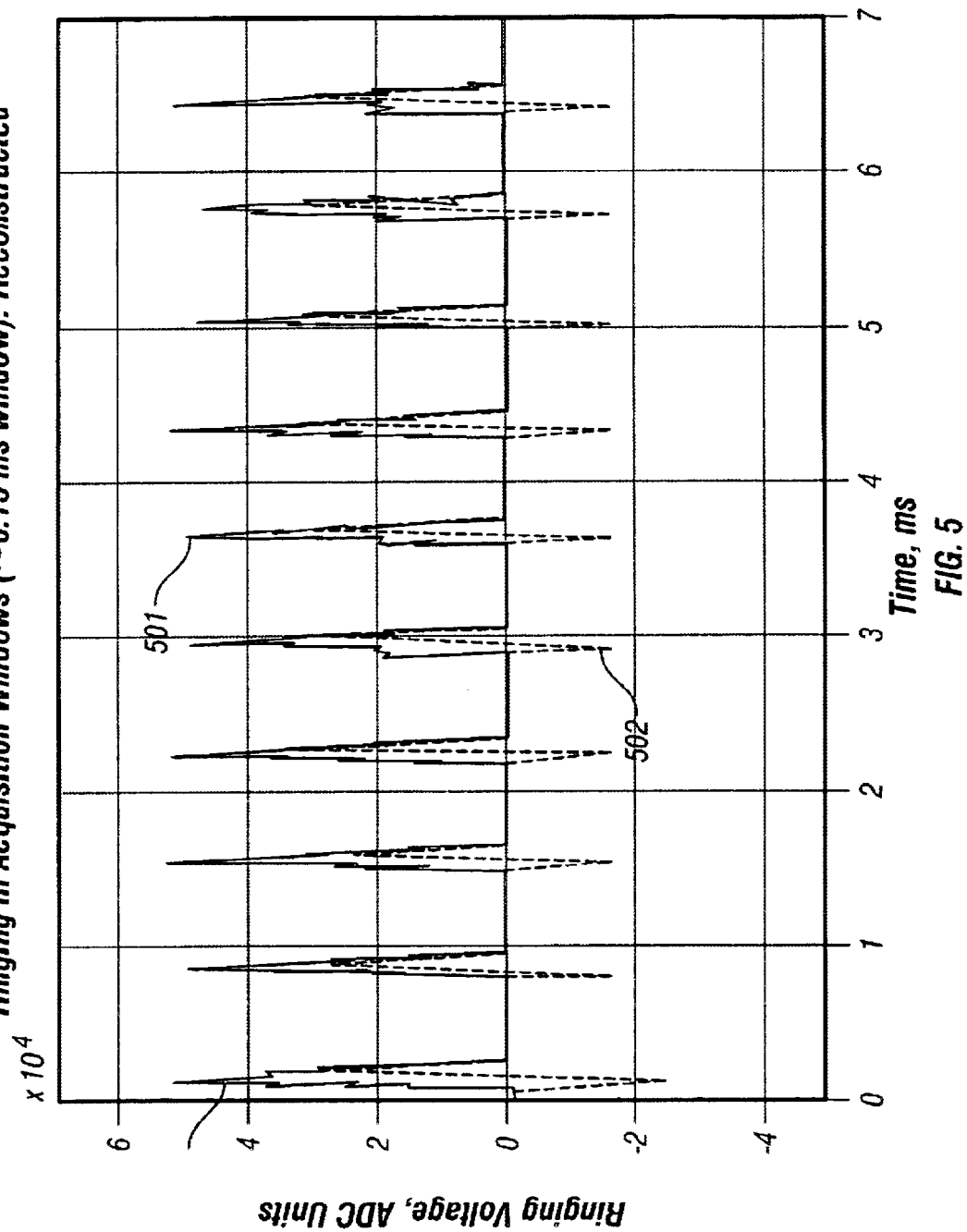
FIG. 5 shows a constructed ringing signal computed according to the method of this invention.
Figure 6:
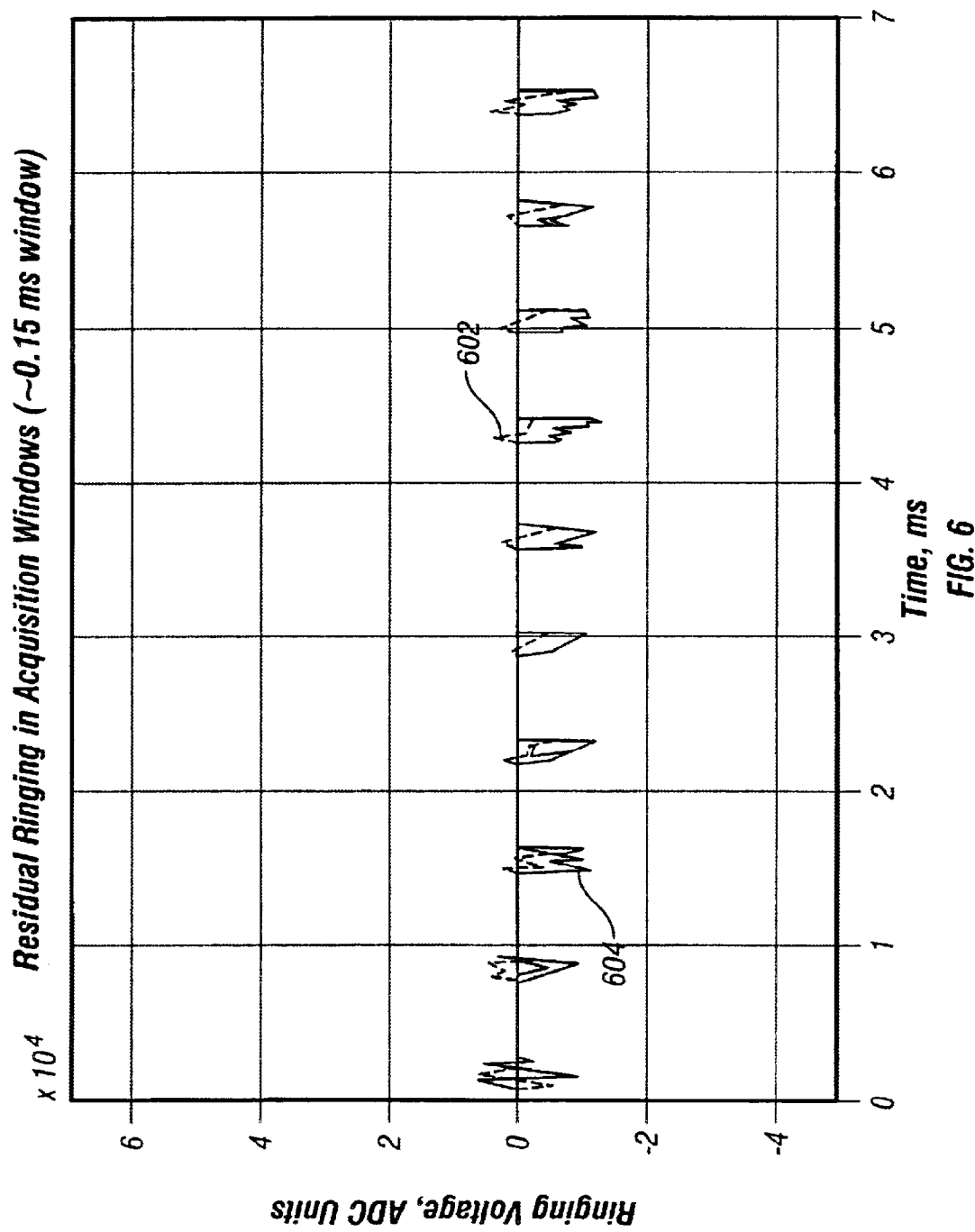
FIG. 6 shows the results of subtracting experiment ringing signal from a ringing signal computed in FIG. 5.

FIG. 5 presents a constructed signal computed according the method defined by Eq. (2). The solid line 501 represents the in-phase component of the signal, and the broken line 502 represents the out-of-phase component of the signal. The signal comprises ringing effects without echo signals. FIG. 6 shows a difference obtained by subtracting the experimental ringing signal shown in FIG. 2 from the reconstructed ringing signal of FIG. 5. As FIGS. 2 and 5 are real and constructed ringing signals, the desired subtraction yields a signal that is substantially zero. The in-phase components are subtracted to yield the solid line 601, which represents the difference in the in-phase components. Similarly, out-of-phase components are subtracted to yield the broken line 602, which represents difference in the out-of-phase components. The residual ringing shown in FIG. 6 is substantially reduced towards zero.

The auxiliary train is typically of short duration compared to the main train and does not add significantly to the power consumption. In a continuously running NMR experiment, the auxiliary train should preferably be started soon after the end of the main train so that the nuclear magnetization can effectively return to equilibrium before, the next CPMG train is activated. To minimally disturb the magnetization it is preferable to employ a forced recovery pulse at the end of the auxiliary train. In this case, the auxiliary pulse train may be described as follows:

$$TW_a - 90_{\pm x} - (t_{cpa} - B_y - t_{cpa})_{N_a} - 90_{\mp x} \quad (3)$$

where, in addition to previously defined terms, $TW_a$ is waiting time before the start of the auxiliary train; $t_{cpa}$ is the time interval between the excitation and refocusing pulses of the auxiliary pulse; $90_{\mp x}$ is the forced recovery pulse; and $N_a$ is the number of repetitions in the auxiliary train.

In practice, a several options are possible for determination of the ringing signals from the excitation pulse and the refocusing pulse. Preferably, the ringing signal caused by the refocusing pulse is obtained using an auxiliary sequence that includes an excitation pulse followed by a refocusing pulse after a sufficiently long time interval (as discussed above so that the ringing caused by the excitation pulse is substantially zero at the time of the first echo following the refocusing pulse). The ringing signal due to the excitation pulse is also preferably obtained using the same auxiliary pulse sequence. Alternatively, the ringing signal due to the excitation pulse is estimated by using an additional auxiliary excitation pulse by itself.

In some practical cases the ringing patterns change relatively slowly compared to the expected changes of the echo signal (due to changing formation). Thus a method can be employed wherein the ringing signal produced by the auxiliary trains is averaged over a relatively long period of time compared to the duration of the echo signal. As the refocusing pulse ringing can be effectively eliminated by phase alternated pulse sequence, this method is more enabling for the excitation pulse ringing acquisition. While the foregoing disclosure is directed to the preferred embodiments of the invention, various modifications will be apparent to those skilled in the art. It is intended that all such variations within the scope and spirit of the appended claims be embraced by the foregoing disclosure.

What is claimed is:

1. A method of obtaining information about an earth formation comprising:

(a) conveying a Nuclear Magnetic Resonance logging tool into a borehole in said earth formation;

(b) obtaining a primary sequence of NMR echo signals sequence in response to a primary applied pulse sequence, said primary pulse sequence comprising an excitation pulse and a plurality of refocusing pulses; and (c) estimating a NMR signal resulting from an auxiliary sequence including, an excitation pulse followed by a refocusing pulse after a time delay, said time delay being sufficiently large so that a non-formation signal caused by the excitation pulse of said auxiliary pulses is substantially zero at the time of an echo resulting from the refocusing pulse and wherein the time delay is different from a time interval between the excitation pulse of the primary pulse sequence and a first one of the plurality of refocusing pulses of the primary pulse sequence; and (d) using said estimate of said non-NMR signal for correcting an echo in said NMR echo signals.

2. The method of claim 1 wherein said correcting further comprises:

(i) constructing a sequence of signals indicative of non-NMR signal from said estimate; and (ii) subtracting said constructed sequence from said primary sequence of NMR signals.

3. The method of claim 2, wherein said constructed sequence further comprises $$R_{X,Y}(t) = W(t) \cdot \left[ R_{90X,Y}(t) + \sum_{i=1}^{N} R_{BX,Y}(t - TE/2 - (i-1) \cdot TE) \right]$$

with $t > TE/2 + (i-1) \cdot TE$, and where $R_{90X,Y}(t)$ is a ringing signal after the excitation pulse with $t=0$ corresponding to the center of the pulse; $R_{BX,Y}(t - TE/2 - (i-1) \cdot TE)$ is a ringing signal obtained after application of the $i^{th}$ refocusing pulse; $W(t)$ is the acquisition window function; N is the number of refocusing pulses used for the ringing signal acquisition; $TE = 2t_{cp}$ is a time interval between the refocusing pulses.

4. The method of claim 1, wherein said primary pulse sequence further comprises a sequence of the form:

$$TW-90_{-x}-[t_{cp}-B_y-t_{cp}-\pm echo]_N$$

where TW is a wait time, $90_{\pm x}$ is an excitation pulse with RF carrier phase alternated, $B_y$ is a refocusing pulse, $t_{cp} = TW/2$ is half of the inter-echo spacing (TE), and N is the number of refocusing pulses.

5. The method of claim 1, wherein said plurality of refocusing pulses further comprises a 180° reorientation pulse.

6. The method of claim 1, wherein said plurality of refocusing pulses further comprises a pulse for reorienting nuclear spins by an angle in a range of about 90 to 180 degrees.

7. The method of claim 1, wherein said non-NMR signal results from at least one refocusing pulse.

8. The method of claim 7, wherein said refocusing pulse further comprises a 180° refocusing pulse.

9. The method of claim 7, wherein said refocusing pulse further comprises a pulse for reorienting atomic nuclei by an angle in a range of about 90 to 180 degrees.

10. The method of claim 1, wherein said one or more auxiliary pulses further comprise the sequence, $$TW_a - 90_{\pm x} - (t_{cpa} - B_y - t_{cpa})_{N_a} - 90_{\mp x}$$

where $TW_a$ is waiting time before the start of the auxiliary train; $90_{\pm x}$ is an excitation pulse with RF carrier phase alternated; $t_{cpa}$ is the time interval between the excitation and refocusing pulses of the auxiliary pulse; $B_y$ is the refocusing pulse; $90_{\mp x}$ is a forced recovery pulse; and $N_a$ is the number of repetitions in the auxiliary train.

11. The method of claim 1 wherein said primary pulse sequence and said auxiliary pulse sequence are applied at substantially the same depth.

12. An apparatus for obtaining information about an earth formation, said apparatus comprising:

(a) a Nuclear Magnetic Resonance (NMR) logging tool conveyed into a borehole in said earth formation;

(b) a receiver on the NMR logging tool obtaining a primary sequence of NMR echo signals sequence resulting from application of a primary applied pulse sequence by a transmitter on said NMR logging tool, said primary pulse sequence comprising an excitation pulse and a plurality of refocusing pulses; and (c) a processor estimating a non-NMR signal resulting from application of an auxiliary pulse sequence by said transmitter, said auxiliary pulse sequence including an excitation pulse followed by a refocusing pulse after a time delay, said time delay being sufficiently large so that a non-NMR signal caused by the preceding excitation pulse is substantially zero at the time of an echo resulting from the refocusing pulse and wherein the time delay is different from a time interval between the excitation pulse of the primary pulse sequence and a first one of the plurality of refocusing pulses of the primary pulse sequence; and wherein said processor further uses said estimate of said non-NMR signal for correcting an echo in said NMR echo signals.

13. The apparatus of claim 12 wherein said correcting further comprises:
   (i) constructing a sequence of signals indicative of a non-NMR signal from said estimate; and
   (ii) subtracting said constructed sequence from said primary sequence of NMR signals.

14. The apparatus of claim 13, wherein said constructed sequence further comprises a sequence of the form:

$$R_{X,Y}(t) = W(t) \cdot \left[ R_{90X,Y}(t) + \sum_{i=1}^{N} R_{BX,Y}(t - TE/2 - (i-1) \cdot TE) \right]$$

with $t > TE/2 + (i-1) \cdot TE$, and where $R_{90X,Y}(t)$ is a ringing signal after the excitation pulse with $t=0$ corresponding to the center of the pulse; $R_{BX,Y}(t - TE/2 - (i-1) \cdot TE)$ is a ringing signal obtained after application of the $i^{th}$ refocusing pulse; W(t) is an acquisition window function; N is a number of refocusing pulses used for the ringing signal acquisition; $TE = 2t_{cp}$ is a time interval between the refocusing pulses.

15. The apparatus of claim 12, wherein said primary pulse sequence further comprises a sequence of the form:

$$TW - 90_{\pm x} - [t_{cp} - B_y - t_{cp} - \pm echo]_N$$

where TW is a wait time, $90_{\pm x}$ is an excitation pulse with RF carrier phase alternated, $B_y$ is a refocusing pulse, $t_{cp} = TW/2$ is half of an inter-echo spacing (TE), and N is the number of refocusing pulses.

16. The apparatus of claim 12, wherein said plurality of refocusing pulses further comprises a 180° reorientation pulse.

17. The apparatus of claim 12, wherein said plurality of refocusing pulses further comprises a pulse for reorienting nuclear spins by an angle in a range of about 90 to 180 degrees.

18. The apparatus of claim 12, wherein said non-NMR signal results from at least one refocusing pulse.

19. The apparatus of claim 12, wherein said one or more auxiliary pulses further comprise the sequence, $$TW_a - 90_{\pm x} - (t_{cpa} - B_y - t_{cpa})_{N_a} - 90_{\mp x}$$

where $TW_a$ is a waiting time before the start of the auxiliary train; $90_{\pm x}$ is an excitation pulse with RP carrier phase alternated; $t_{cpa}$ is a time interval between the excitation and refocusing pulses of the auxiliary pulse; $B_y$ is the refocusing pulse; $90_{\mp x}$ is a forced recovery pulse; and $N_a$ is the number of repetitions in the auxiliary train.

20. The apparatus of claim 12 wherein said primary pulse sequence and said auxiliary pulse sequence are applied at substantially the same depth.

21. A method of obtaining information about an earth formation comprising:
   (a) conveying a Nuclear Magnetic Resonance logging tool into a borehole in said earth formation;
   (b) obtaining a primary sequence of NMR echo signals sequence in response to a primary applied pulse sequence, said primary pulse sequence comprising an excitation pulse and a plurality of refocusing pulses;
   (c) estimating a non-formation signal resulting from a single auxiliary pulse, and
   (d) using said estimate of said non-formation signal for removing ringing in said primary sequence of NMR echo signals resulting from the excitation pulse of said primary pulse sequence and at least one of the plurality of refocusing pulses of the primary pulse sequence.

22. The method of claim 21 wherein said removing further comprises:
   (i) constructing a sequence of signals indicative of said non-formation signal from said estimate; and
   (ii) subtracting said constructed sequence from said primary seqence of NMR echo signals.

23. The method of claim 22, wherein said constructed sequence further comprises $$R_{X,Y}(t) = W(t) \cdot \left[ R_{90X,Y}(t) + \sum_{i=1}^{N} R_{BX,Y}(t - TE/2 - (i-1) \cdot TE) \right]$$

with $t > TE/2 + (i-1) \cdot TE$, and where $R_{90X,Y}(t)$ is a ringing signal after the excitation pulse with $t=0$ corresponding to the center of the pulse; $R_{BX,Y}(t - TE/2 - (i-1) \cdot TE)$ is a ringing signal obtained after application of the $i^{th}$ refocusing pulse; W(t) is the acquisition window function; N is the number of refocusing pulses used for the ringing signal acquisition; $TE = 2t_{cp}$ is a time interval between the refocusing pulses.

24. The method of claim 21, wherein said primary pulse sequence further comprises a sequence of the form:

$$TW - 90_{\pm x} - [t_{cp} - B_y - t_{cp} - \pm echo]_N$$

where TW is a wait time, $90_{\pm x}$ is an excitation pulse with RF carrier phase alternated, $B_y$ is a refocusing pulse, $t_{cp} = TW/2$ is half of an inter-echo spacing (TE), and N is the number of refocusing pulses.

25. The method of claim 21, wherein said plurality of refocusing pulses of the primary pulse sequence further comprises a 180° reorientation pulse.

26. The method of claim 21, wherein said plurality of refocusing pulses of the primary pulse sequence further comprises a pulse for reorienting nuclear spins by an angle in a range of about 90° to 180°.

27. The method of claim 21 wherein said primary pulse sequence and said single auxiliary pulse are applied at substantially the same depth.

28. The method of claim 21 wherein said single auxiliary pulse comprises a refocusing pulse.

29. An apparatus for obtaining information about an earth formation, said apparatus comprising:
   (a) a Nuclear Magnetic Resonance (NMR) logging tool conveyed into a borehole in said earth formation;
   (b) a receiver on the NMR logging tool for obtaining a primary sequence of NMR echo signals sequence resulting from application of a primary applied pusle sequence by a transmitter on said NMR logging tool, said primary pulse sequence comprising an excitation pulse and a plurality of refocusing pulses; and
   (c) a processor for estimating a non-formation signal resulting from application of a single auxiliary pulse; and wherein said processor further uses said estimate of said non-formation signal for removing ringing in said primary sequence of NMR echo signals resulting from the excitation pulse of the primary pulse sequence and the plurality of refocusing pulses of the primary pulse sequence.

30. The apparatus of claim 29 wherein said removing further comprises:
(i) constructing a sequence of signals indicative of said non-formation signal from said estimate; and
(ii) substracting said constructed sequence from said primary sequence of NMR signals.

31. The method of claim 29, wherein said constructed sequence further comprises a sequence of the form:

$$R_{X,Y}(t) = W(t) \cdot \left[ R_{90X,Y}(t) + \sum_{i=1}^{N} R_{BX,Y}(t - TE/2 - (i-1) \cdot TE) \right]$$

with $t > TE/2 + (i-1) \cdot TE$, and where $R_{90X,Y}(t)$ is a ringing signal after the excitation pulse with t=0 corresponding to the center of the pulse; $R_{BX,Y}(t-TE/2-(i-1) \cdot TE)$ is a ringing signal obtained after application of the $i^{th}$ refocusing pulse; W(t) is the acquisition window function; N is the number of refocusing pulses used for the ringing signal acquisition; $TE=2t_{cp}$ is a time interval between the refocusing pulses.

32. The apparatus of claim 29 wherein said auxiliary pulse comprises an excitation pulse.

33. The apparatus of claim 29 wherein said primary pulse sequence and said single auxiliary pulse are applied at substantially the same depth.

34. The apparatus of claim 29 wherein said single auxiliary pulse comprises a refocusing pulse.

* * * * *